US00PP16806P2

(12) United States Plant Patent
Brown

(10) Patent No.: US PP16,806 P2
(45) Date of Patent: Jul. 11, 2006

(54) ***PETUNIA* PLANT NAMED 'MPD2'**

(50) Latin Name: *Petunia×hybrida*
Varietal Denomination: MPD2

(75) Inventor: Graham Noel Brown, Pennant Hills (AU)

(73) Assignee: NuFlora International Pty. Ltd., Macquarie Fields (AU)

( * ) Notice: Subject to any disclaimer, the term of this patent is extended or adjusted under 35 U.S.C. 154(b) by 15 days.

(21) Appl. No.: 11/091,808

(22) Filed: Mar. 28, 2005

(51) Int. Cl.
*A01H 5/00* (2006.01)

(52) U.S. Cl. ..... Plt./356
(58) Field of Classification Search ..... Plt./356
See application file for complete search history.

*Primary Examiner*—Anne Marie Grunberg
*Assistant Examiner*—Annette H Para
(74) *Attorney, Agent, or Firm*—C. A. Whealy

(57) ABSTRACT

A distinct cultivar of *Petunia* plant named 'MPD2', characterized by its compact, outwardly spreading and cascading plant habit; freely branching habit; and numerous small double flowers that are light purple in color with dark violet-colored venation.

1 Drawing Sheet

Botanical designation: *Petunia×hybrida.*
Cultivar denomination: 'MPD2'.

BACKGROUND OF THE INVENTION

The present Invention relates to a new and distinct cultivar of *Petunia* plant, botanically known as *Petunia×hybrida*, and hereinafter referred to by the cultivar name MPD2.

The new *Petunia* is a product of a planned breeding program conducted by the Inventor in Cobbitty, New South Wales, Australia. The objective of the breeding program is to create new *Petunias* with numerous small double flowers with attractive flower colors.

The new *Petunia* originated from a cross-pollination made by the Inventor in December, 2001 of a proprietary *Petunia×hybrida* selection identified as X01.154.3, not patented, as the female, or seed parent, with a proprietary *Petunia×hybrida* selection identified as PKC27, not patented, as the male, or pollen parent. The new *Petunia* was selected as a single plant from the resulting progeny of the cross-pollination by the Inventor in a controlled environment in Cobbitty, New South Wales, Australia in October, 2002.

Asexual reproduction of the new cultivar by terminal cuttings in a controlled environment in Cobbitty, New South Wales, Australia since October, 2002 has shown that the unique features of this new *Petunia* are stable and reproduced true to type in successive generations.

SUMMARY OF THE INVENTION

Plants of the cultivar MPD2 have not been observed under all possible environmental conditions. The phenotype may vary somewhat with variations in environment such as temperature and light intensity without, however, any variance in genotype.

The following traits have been repeatedly observed and are determined to be the unique charcteristics of 'MPD2'. These chacteristics in combination distinguish 'MPD2' as a new and distinct *Petunia* cultivar:

1. Compact, outwardly spreading and cascading plant habit.

2. Freely branching habit.
3. Numerous small double flowers that are light purple in color with dark violet-colored venation.

Plants of the *Petunia* differ primarily from plants of the female parent selection in flower form as plants of the female parent selection have single flowers. Compared to plants of the male parent selection, plants of the new *Petunia* are more compact and have a more spreading plant habit. In addition, plants of the new *Petunia* differ primarily from plants of the male parent selection in flower coloration as plants of the male parent selection have white-colored flowers.

Plants of the new *Petunia* can be compared to plants of the cultivar Tedropur, disclosed in U.S. Plant Pat. No. 14,179. In side-by-side comparisons conducted in Cobbitty, New South Wales, Australia, plants of the new *Petunia* differed from plants of the cultivar Tedropur in the following characteristics:

1. Plants of the new *Petunia* were more spreading than plants of the cultivar Tedropur.
2. Plants of the new *Petunia* and the cultivar Tedropur differed in flower coloration as plants of the cultivar Tedropur have purple violet-colored flowers.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Petunia.*

The photograph at the bottom of the sheet comprises a side perspective view of a typical flowering plant of 'MPD2' grown in a container.

The photograph at the top of the sheet comprises a close-up view of typical flowers and leaves of 'MPD2'.

DETAILED BOTANICAL DESCRIPTION

The aforementioned photographs and following observations and measurements describe plants grown in Lompoc, Calif., under commercial practice during the winter and early spring in a polycarbonate-covered greenhouse with day temperatures ranging from 21 to 24° C., night temperatures ranging from 16 to 18° C., and light levels ranging from 5,000 to 9,000 foot candles. Plants were grown for about 14 weeks with one plant per 14-cm container. In the following description, color references are made to The Royal Horticultural Society Colour Chart, 1995 Edition, except where general terms of ordinary dictionary significance are used.

Botanical Classification: *Petunia×hybrida* cultivar MPD2.

Parentage:

*Female parent.*—Proprietary *Petunia×hybrida* selection identified as X01.154.3, not patented.

*Male parent.*—Proprietary *Petunia×hybrida* selection identified as PKC27, not patented.

Propagation:

*Type cutting.*—Terminal vegetative cuttings.

*Time to initiate roots.*—About 10 days at 22° C.

*Time to produce a rooted young plant.*—About three weeks at 22° C.

*Root description.*—Fine, fibrous; white in color.

*Rooting habit.*—Freely branching; dense.

Plant description:

*Plant shape and habit.*—Annual flowering plant; indeterminate; compact; initially upright, then low, outwardly spreading and cascading plant habit; plants eventually becoming hemispherical to spherical in shape. Viscid and glandular pubescent. Vigorous growth habit.

*Branching habit.*—Freely branching with about eight main branches each with lateral branches potentially at every node.

*Plant height.*—About 16 cm.

*Plant diameter.*—About 38 cm.

*Lateral branches.*—Length: About 32 cm. Diameter: About 2.5 mm. Internode length: About 1.1 cm. Texture: Pubescent. Color: 145A.

*Foliage description.*—Arrangement: Before flowering commences: Alternate, simple. After flowering commences: Opposite; simple. Length: About 2.7 cm. Width: About 1.5 cm. Shape: Elliptical. Apex: Rounded to broadly acute. Base: Attenuate. Margin: Entire. Texture, upper and lower surfaces: Slightly pubescent; glandular. Venation pattern: Pinnate; arcuate. Color: Developing foliage, upper and lower surfaces: 144A. Fully expanded foliage, upper surface: 146A. Fully expanded foliage, lower surface: 146B. Venation, upper and lower surfaces: 146B. Petiole length: About 7 mm. Petiole diameter: About 2 mm. Petiole texture: Sparsely pubescent. Petiole color: 144B.

Flower description:

*Flower type and habit.*—Double flowers; flowers face mostly upward or outward; axillary. Flowers persistent. Very freely flowering, about 24 open flowers and flower buds per lateral branch.

*Natural flowering season.*—Long day responsive; spring until frost in the autumn; flowering continuous.

*Flower longevity on the plant.*—About seven to ten days.

*Fragrance.*—Light, spicy, floral.

*Flower size.*—Diameter: About 3 cm. Height (depth): About 3 cm. Tube length: About 1.8 cm. Throat diameter, distal end: About 3 mm. Tube diameter, proximal end: About 3 mm.

*Flower buds* (*showing color*).—Length: About 2 cm. Diameter: About 6 mm. Shape: Obovate. Color: 145D.

*Corolla.*—Quantity/arrangement: About seven fused outer petals, funnelform; interior to outer whorl, about five fused petaloids; at center, about six free petaloids. Petal length from throat: About 1.3 cm. Petal width: About 1 cm. Petal/petaloid shape: Roughly obovate or spatulate. Petal/petaloid apex: Rounded. Petal/petaloid margin: Entire; sinuate. Petal/petaloid texture, upper and lower surfaces: Smooth, velvety. Color: Petal/petaloid, upper surface, when opening: 86D; venation, 79A. Petal/petaloid, lower surface, when opening: 75C; venation, 77A. Petal/petaloid, upper surface, fully opened: 76B; venation, 86A. Petal/petaloid, lower surface, fully opened: 76C to 76D; venation, 77A. Flower throat (inside): 79A; venation, 79A. Flower tube (outside): 144A; venation, 79B.

*Sepals.*—Arrangement/appearance: Single whorl of five sepals fused at base, star-shaped. Length: About 1 cm. Width: About 2.5 mm. Shape: Linear. Apex: Rounded. Margin: Entire. Texture, upper and lower surfaces: Pubescent. Color, upper surface: 146A. Color, lower surface: 146B.

*Peduncles.*—Length: About 2 cm. Width: About 1 mm. Angle: About 45° from the stem. Strength: Strong. Texture: Pubescent. Color: 146A.

*Reproductive organs.*—Stamens: None observed, transformed into petaloids. Pistils: Quantity: One per flower. Pistil length: About 2 mm. Stigma shape: Bi-lobed, somewhat asymmetrical. Stigma color: 145D. Style length: About 1.5 mm. Style color: 145A. Ovary color: 145C.

*Fruit/seed.*—Fruit and seed production has not been observed.

Disease/pest resistance: Plants of the new *Petunia* have not been noted to be resistant to pathogens or pests common to *Petunia*.

Temperature tolerance: Plants of the new *Petunia* have been observed to tolerate temperatures from 4 to 34° C.

It is claimed:

1. A new and distinct cultivar of *Petunia* plant named 'MPD2', as illustrated and described.

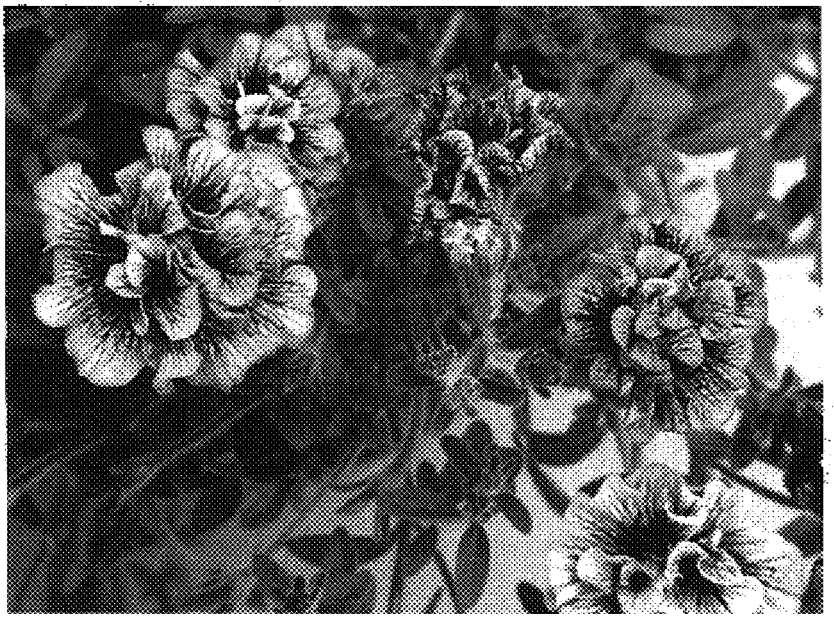
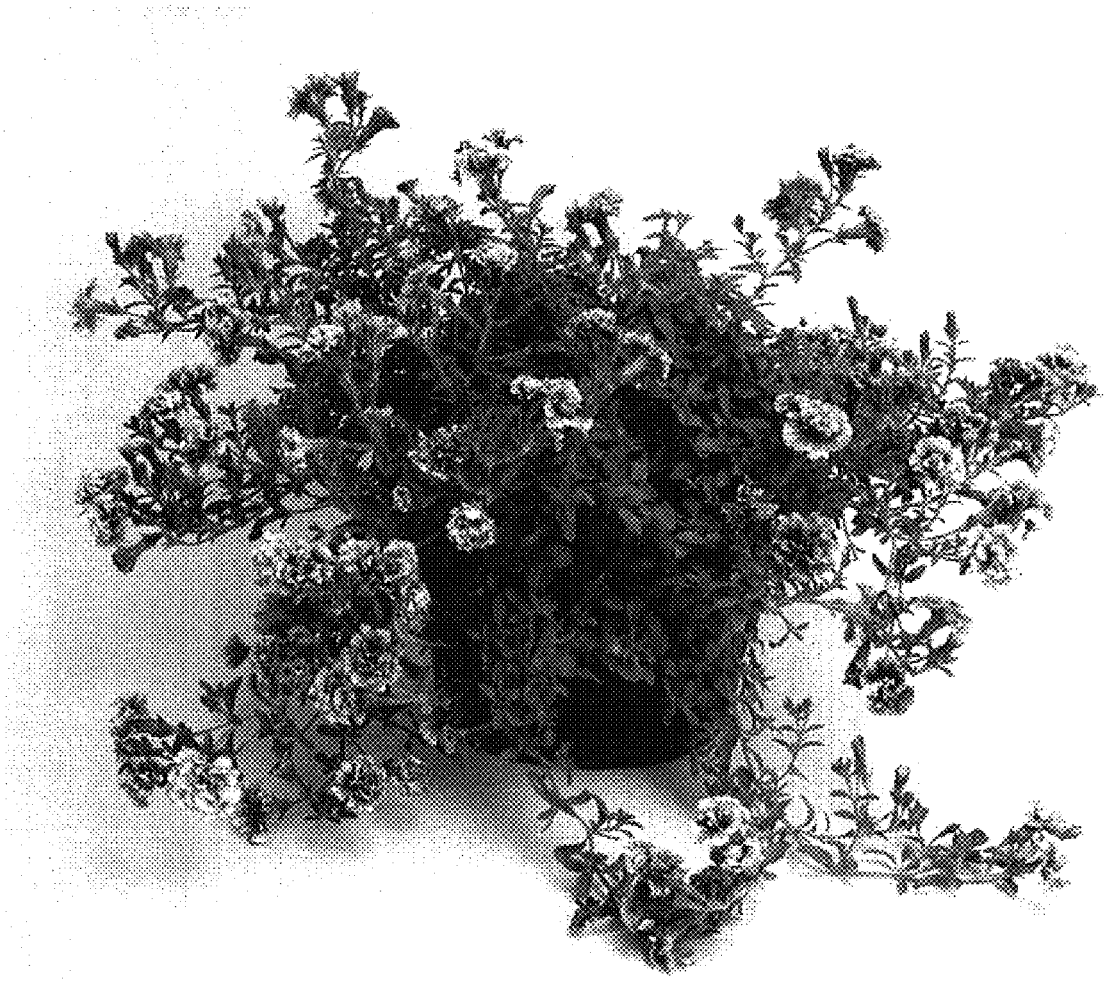

* * * * *